United States Patent [19]

Talley

[11] Patent Number: 5,473,092
[45] Date of Patent: Dec. 5, 1995

[54] SYNTHESIS OF OPTICALLY-ACTIVE PHOSPHONO ANALOGS OF SUCCINATES

[75] Inventor: John J. Talley, St. Louis, Mo.

[73] Assignee: Monsanto Company, St. Louis, Mo.

[21] Appl. No.: 396,996

[22] Filed: Mar. 1, 1995

Related U.S. Application Data

[62] Division of Ser. No. 979,735, Nov. 20, 1992, abandoned.

[51] Int. Cl.$^6$ .................................. C07F 9/38; C07F 9/40
[52] U.S. Cl. ............................................. 558/87; 558/179
[58] Field of Search .................................................. 558/87

[56] References Cited

U.S. PATENT DOCUMENTS 4,939,288  7/1990  Talley ........................................ 560/81

OTHER PUBLICATIONS

Vineyard, B. D. et al. "Asymmetric Hydrogenation. Rhodium Chiral Bisphosphine Catalyst" *J. Am. Chem. Soc.* 1977, 99(18), 5946–52.

*Primary Examiner*—Johann Richter
*Assistant Examiner*—Michael G. Ambrose
*Attorney, Agent, or Firm*—Frank S. Ungemach; Joan Thierstein

[57] ABSTRACT

The present invention relates to catalytic asymmetric hydrogenation of phosphorus analogs of itaconic acid to synthesize novel optically active phosphono succinates.

6 Claims, No Drawings

SYNTHESIS OF OPTICALLY-ACTIVE PHOSPHONO ANALOGS OF SUCCINATES

This is a division of application Ser. No. 07/979,735 filed Nov. 20, 1992, now abandoned.

BACKGROUND OF THE INVENTION

The present invention relates to catalytic asymmetric hydrogenation of phosphorus analogs of itaconic acid to synthesize novel optically active phosphono succinates. These are essentially pure novel phosphono succinates having optical activity and are useful as intermediates for the preparation of phosphorus containing pseudopeptides having physiological activity, for example, pharmacological activity. See J. Med. Chem. 31, pp. 1772 (1988).

Preparation of optically active compounds by asymmetric hydrogenation are included in the copending applications U.S. Ser. No. 07/898,853 filed Jun. 15, 1992 and U.S. Ser. No. 07/898,253 filed Jun. 15, 1992. These applications review relevant references and are, therefore, hereby incorporated by reference.

Copending application U.S. Ser. No. 07/898,853 discloses chiral alpha-amino ketones in which the —CONH— linkage has been replaced by a —COCH$_2$— and a process for the preparation which provides a wide range of side chains. Copending application U.S. Ser. No. 07/898,253 discloses both novel alpha-amino phosphonates and a process having sufficient flexibility for use in making the phosphonates. However, the present invention uses phosphorus analogs of itaconic acid to provide novel compounds and process therefor.

The following references relate to the preparation of optically active succinic acid derivatives: JP 54122219-A abstracted in Derwent No. 79835B/44; JP 54057490-A abstracted in Derwent No. 46194/25; JP 54128511-A abstracted in Derwent No. 83174/46; JP 3101638 abstracted in Derwent No. 91-168387/23. U.S. Pat. No. 4,922,006 discloses the hydrogenation of 2,3-dehydrophosphinothricine derivatives using a ruthenium, rhodium or iridium complex of phosporus containing catalyst. U.S. Pat. No. 4,939,288 discloses asymmetric catalytic hydrogenation of a 2(E)-alkylidene succinate derivative in the presence of a rhodium complexed (R,R)-bisphosphine compound.

U.S. Pat. No. 4,016,148 discloses peptide derivatives having a moiety characterized by the replacement of the carboxyl group of a naturally occurring L alpha-amino acid by a phosphorus group including a —P(O)(OH)$_2$ group.

Optically active alpha-amino phosphonates are useful as antibiotics and/or are useful in the preparation of phosphorus-containing analogs of peptides, i.e., —P(O)(OH)$_2$ replaces a —CONH$_2$ group to provide phosphono peptides or pseudopeptides, having known uses. For example, such phosphorus-type compounds have been shown to be effective as antibiotics, antibiotic enhancers, or enzyme inhibitors.

The flexibility of the present synthesis permits the synthesis of analogues of unexpectedly pure chiral phosphono succinate derivatives, ie a peptide-like compound having the —CONH— replaced by —COCH$_2$— and another amino group replaced by a phosphono group, also having a wide range of substituents.

As discussed above the literature is replete with examples of novel amino acid side chains designed to impart improved biological properties to peptides and pseudopeptide molecules. Thus, the present novel compounds are useful as intermediates to make products or may be themselves products having such biological properties.

BRIEF SUMMARY OF THE INVENTION

The present invention is a novel compound of the formula (I)

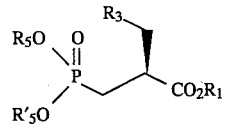

wherein R$_1$ is hydrogen, alkyl, lower cycloalkyl, or Ar wherein Ar is an aromatic group, preferably CH$_2$Ar, including, particularly, unsubstituted or substituted phenylmethyl;

R$_3$ is (1) hydrogen;
(2) alkyl of from 1 to 6 carbons optionally substituted by one or two hydroxyl, chloro or fluoro;
(3) cycloalkyl of from 3 to 7 ring carbons;
(4) Ar$_4$ which is a group such as phenyl, or phenyl substituted by one to three substituent(s) consisting of
   (a) alkyl of from one to four carbons,
   (b) halogen consisting of fluoro, chloro, bromo, iodo,
   (c) alkoxy of from one to three carbons,
   (d) nitro,
   (e) amido,
   (f) mono- or di- alkyl (of from one to four carbons)amido, or
   (g) hydroxy;
(5) Ar$_5$ which is tolyl;
(6) Ar$_6$ which is tolyl substituted by one to three substituents consisting of
   (a) alkyl of from of one to four carbons,
   (b) halogen consisting of fluoro, chloro, bromo. iodo,
   (c) alkoxy of from one to three carbons,
   (d) nitro,
   (e) amido,
   (f) mono- or di- alkyl (of from one to four carbons) amido, or
   (g) hydroxy;
(7) Ar$_7$ which is naphthyl or naphthyl substituted by one to three substituents consisting of
   (a) alkyl of from one to four carbons,
   (b) halogen consisting of fluoro, chloro, bromo, iodo,
   (c) alkoxy of from one to three carbons,
   (d) nitro,
   (e) amido,
   (f) mono- or di- alkyl (of from one to four carbons) amido, or
   (g) hydroxy;
(8) Ar$_8$ which is a group such as indol-3 -yl, indol-2-yl, or imidazoly-4-yl or indol-3-ylmethyl, indol-2-ylmethyl or imidazol-4-ylmethyl (preferably unsubstituted or substituted phenyl or indol-3-yl);
(9) NHA wherein A is
   (a) trityl,
   (b) hydrogen,
   (c) alkyl of from one to six carbons,
   (d) R$_{10}$CO wherein R$_{10}$ is (A)hydrogen, (B) alkyl of from one to six carbons optionally substituted with hydroxyl, chloro, or fluoro, (C) phenyl or naphthyl; unsubstituted or substituted with one to three of (i) alkyl of from one to three carbons, (ii) halogen where halogen is F, Cl, Br, or I, (iii)

hydroxy, (iv) nitro, (v) alkoxy of from one to three carbons, (vi) $CON(R_{11})_2$ wherein $R_{11}$ is independently hydrogen or alkyl of from one to four carbons, or (D) a 5 to 7 member heterocycle such as indolyl, pyridyl, furyl or benzisoxazolyl;

(e) phthaloyl wherein the aromatic ring is optionally substituted by one to three of (A) alkyl of from to three carbons, (B) halogen where halogen is F, Cl, Br, or I, (C) hydroxy, (D) nitro, (E) alkoxy of from one to three carbons, (F) $CON(R_{11})_2$ wherein $R_{11}$ is independently hydrogen or alkyl of from one to four carbons, (f) $R_{12}(R_{13}R_{14}C)_mCO$ wherein m is one to three and $R_{12}$, $R_{13}$, and $R_{14}$ are independently (A) hydrogen, (B) chloro or fluoro, (C) alkyl of from one to three carbons optionally substituted by chloro, fluoro, or hydroxy, (D) hydroxy, (E) phenyl or naphthyl optionally substituted by one to three of (i) alkyl of from to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons, (F) alkoxy of from one to three carbons, (G) 5 to 7 member heterocycle such as pyridyl, furyl, or benzisoxazolyl, or (H) $R_{12}, R_{13}$, and $R_{14}$ are independently joined to form a monocyclic, bicyclic, or tricycle ring system each ring of which is a cycloalkyl of from three to six carbons, except that only one of $R_{12}$, $R_{13}$ and $R_{14}$ can be hydroxy or alkoxy on the same carbon and can not be hydroxy, chloro or fluoro when m is one;

(g) $R_{12}(R_{13}R_{14}C)_mW$ wherein m is independently 1 to 3 and W is OCO or $SO_2$ and $R_{12}$, $R_{13}$, and $R_{14}$ are independently as defined above;

(h) $R_{20}W$ wherein $R_{20}$ is a 5 to 7 member heterocycle such as pyridyl, furyl, or benzisoxazolyl and W is as defined above;

(i) $R_{21}W$ wherein $R_{21}$ is phenyl or naphthyl; unsubstituted or substituted by one to three substituents of (A) alkyl of from to three carbons, (B) halogen where halogen is F, Cl, Br, or I, (C) hydroxy, (D) nitro, (E) alkoxy of from one to three carbons, (F) $CON(R_{11})_2$ wherein $R_{11}$ is independently hydrogen or alkyl of from one to four carbons and W is as defined above;

(j) $R_{12}(R_{13}R_{14}C)_mP(O)(OR_{22})$ wherein $R_{22}$ is alkyl of from one to four carbons or phenyl and m is as defined above;

(k) $R_{20}P(O)(OR_{22})$ wherein $R_{20}$ and $R_{22}$ are as defined above;

(l) $R_{21}P(O)(OR_{22})$ wherein $R_{20}$ and $R_{22}$ are as defined above;

(10) $R_{12}(R_{13}R_{14}C)_mV$ wherein V is O or NH and $R_{12}(R_{13}R_{14})_m$ are independently as defined above;

(11) $N(R_{11})_2$ wherein $R_{11}$ is independently as defined above;

(12) $NR_{15}N_{16}$ wherein $R_{15}$ and $R_{16}$ are joined to form a 4 to 6 membered saturated nitrogen containing heterocycle which is (A) azetidinyl, (B) pyrrolidinyl, (C) piperidinyl, or (D) morpholinyl;

(13) $R_{17}OCH_2O$ wherein $R_{17}$ is
 (a) alkyl of from one to six carbons,
 (b) $R_{21}$ wherein $R_{21}$ is independently defined as above; or
 (c) $CH_2Q_1$ wherein $Q_1$ is phenyl, naphthyl or a 5 to 7 membered heterocycle;

(14) $R_{17}OCH_2CH_2OCH_2$ wherein $R_{17}$ is independently as defined above;

(15) alkynyl of from two to six carbons optionally substituted with $R_{21}$ where in $R_{21}$ is independently as defined above;

(16) alkenyl of from two to six carbons optionally substituted with $R_{21}$ where in $R_{21}$ is independently as defined above; and

(17) preferably, the amino acid side chains selected from the group consisting of aspargine, 5-methyl cysteine and the corresponding sulfoxide and sulfone derivatives thereof, leucine, isoleucine, alloisoleucine, tert-leucine, alanine, phenylalanine, ornithine, histidine, norleucine, glutamine, valine, threonine, allo-threonine, serine, aspartic acid and beta-cyanoalanine side chains;

$R_5$ and $R_5'$ are, independently, hydrogen, alkyl, lower cycloalkyl, or ar wherein Ar is an aromatic group, preferably unsubstituted or substituted phenyl.

The present invention is also a process for the treatment of a compound of the formula (II)

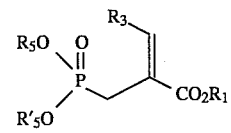

wherein $R_1$, $R_5$ and $R_5'$ is as defined above;
$R_3$ is as defined above; or isomeric mixtures thereof;
with hydrogen in the presence of rhodium (R,R)-( 1,2-ethanediyl bis[ortho-methoxyphenyl)phenylphosphine] ($H_2RhDiPAMP$) in deoxygenated solvent; and
optionally hydrolyzing the phosphorus or carbon containing acid group to obtain a compound of the formula I wherein $R_1$, $R_3$, $R_5$, and $R_5'$ are as defined above.

The present invention is selected compounds of the formula (II)

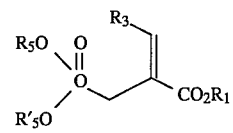

wherein $R_1$, $R_3$, $R_5$ and $R_5'$ are as defined above.

Unpredictably the process of the present invention successfully hydrogenates the Z olefin in the presence of rhodium DiPAMP. Therefore, the reduction of isomeric mixtures of the compounds of the formula II selectively produces compounds of formula I having an S configuration as shown above. This isomer can thus be separated from the unreduced isomer of the original isomeric mixture.

DETAILED DESCRIPTION OF THE INVENTION $C_1$–$C_3$ or –$C_4$ means alkyl of from one to three or four such as methyl, ethyl, propyl or butyl and isomers thereof and the like.

$C_3$–$C_7$ cycloalkyl means cyclic hydrocarbon groups containing 3 to 7 carbon atoms, such as cyclopropyl, cyclobutyl, cyclopentyl, cyclohexyl, methyl cylopentyl, methyl cyclohexyl, dimethyl cyclopentyl, cycloheptyl and the like.

Ar is an aromatic group which means a phenyl, substituted phenyl, tolyl, substituted tolyl, naphthyl and the like.

Substituted phenyl and substituted tolyl means from one to three substituents such as alkyl, carboxyl, hydroxyl (and base salts thereof), alkoxy, halogen which means fluoro, chloro, bromo, or iodo, $C_2$–$C_4$ acyloxy, aryloxy, aralkoxy, amino, alkyl amido (both mono and di alkylamido), nitro, cyano.

Chiral means having optical activity.

Generally, the process comprising the treatment of the compound of formula II with hydrogen in the presence of (R$_1$R) DiPAMP to obtain the compound of the formula I is as set out in Scheme 1 hereinafter.

Scheme 1

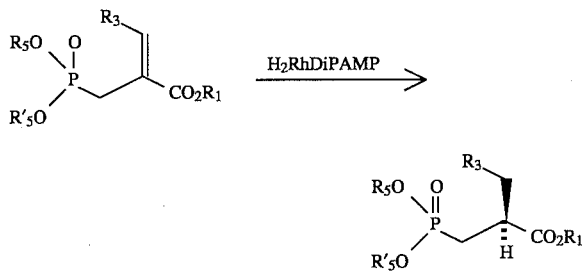

The reaction is accomplished at from about 1 to 100 psig and at a temperature from about 0° C. to 60° C. preferably at about room temperature and at a pressure about 40 psig, in inert solvents such as methanol, ethanol, tetrahydrofuran, dichloromethane, acetonitrile and the like or mixtures thereof.

Evaluation of the results may be accomplished by standard methods, such as vapor phase chromatography on a chiral capillary column, or by HPLC (high performance liquid chromatography) on a chiral column or by evaluation of the optical rotation of a solution of the compound.

A Fisher-Porter bottle is charged with the appropriate substrate dissolved in deoxygenated methanol along with 0.1–1.0 mol percent rhodium (R, R)-DiPAMP (R,R)-(1,2-ethanediyl bis[(o-methoxyphenyl)phenylphosphine]. After 5 nitrogen purges (40 psig) the solution was purged 5 times with hydrogen (40 psig) and then allowed to hydrogenate at room temperature for 1–24 h. The hydrogen was replaced with nitrogen and the contents of the bottle concentrated in vacuo. The catalyst residue was separated from the chiral phosphono succinates of the formula I by dissolving the product in iso-octane. The catalyst residue is not soluble in iso-octane.

A general procedure for the hydrolysis of chiral phosphono succinates of the formula I wherein R$_1$, R$_5$ or R$_5$' is other than hydrogen is as follows. A sample of the chiral phosphono succinate derivative is refluxed for 24 h with 12N hydrochloric acid. The solvent is removed in vacuo. The residue is taken-up in water and re-concentrated in vacuo. The precipitated phosphono succinic acid is then isolated by filtration and optionally recrystallized from water/methanol.

An evaluation is made of optical purity by chiral vapor phase chromatography. The phosphono succinate derivatives are analyzed by chiral gas chromatography for optical purity. A solution of the racemic phosphono succinate derivative in dichloromethane is separated into the two enantiomers by a 25 meter Chirasil Val III capillary column with flame ionization detection. After conditions for separation of the two enantiomers are established, each chiral hydrogenation product is evaluated for the extent of optical purity.

Compounds of the formula II are prepared by methods known in the art or by methods analogous to those known in the art from starting material which are known or which can be prepared by known methods (See references set out in the examples hereinafter).

Variations in these conditions and evaluations for different compounds within the definitions of the formula I are within the skill of an ordinarily skilled artisan. For example, protecting groups may be needed and are utilized as recognized by an ordinarily skilled artisan.

The general procedure for removal of an ester group on either the carboxyl or phosphono group, such as the alkyl, cycloalkyl or aromatic, or specifically tert-butyl ester is as follows. A sample of the product, I, is dissolved in methanol and treated with an equal (volume) amount of sodium hydroxide 0° C. The solution is allowed to warm to room temperature and the progress of the reaction monitored by TLC. When the reaction is finished the solvents are removed in vacuo and the residue purified by crystallization or flash chromatography on silica gel. This procedure produces the acid derivatives.

The compounds of the Formula I are useful as intermediates in the preparation of pharmacologically active compounds. It is contemplated that certain intermediates disclosed herein will manifest similar activity.

The compounds of Formula I, that may be pharmacologically active, are useful both in the free base and the free acid form or in the form of base salts thereof, as well as, in the form of acid addition salts. All forms are within the scope of the invention. In practice, use of the salt form amounts to use of the free acid or free base form. Appropriate pharmaceutically acceptable salts within the scope of the invention are those derived from mineral and organic acids or those derived from bases such as suitable organic and inorganic bases. For example, see "Pharmaceutical Salts" *J. Pharm Sci.*, 66(1), 1–19 (1977). The acid addition salts of said compounds are prepared either by dissolving the free base of compound I in aqueous or aqueous alcohol solution or other suitable solvents containing the appropriate acid or base and isolating the salt by evaporating the solution, or by reacting the free base of Compound I with an acid as well as reacting compound I having an acid group thereon with a base such that the reactions are in an organic solvent, in which case the salt separates directly or can be obtained by concentration of the solution.

The base salts of compounds of Formula I described above are prepared by reacting the appropriate base with a stoichiometric equivalent of the acid compounds of Formula I to obtain pharmacologically acceptable base salts thereof.

Contemplated equivalents of the general formulas set forth above for the compounds I as well as the compounds useful to prepare compounds I are compounds otherwise corresponding thereto and having the same general properties wherein one or more of the various R groups are simple variations of the substituents as defined therein, e.g., wherein R$_1$, R$_5$ or R$_5$' is a higher alkyl group. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Example 1

Preparation of Methyl 2-[(dimethoxyphosphoryl)methyl] propenoate.

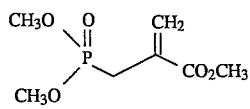

Dimethylphosphite (5.0 mL, 54 mmol) was dissolved in 150 mL of methanol cooled to 0° C. and then treated by the dropwise addition of a solution of sodium methoxide (65 mmol) in 150 mL of methanol. After the addition was complete, the solution was stirred at 0° C. for 15 min and then treated with a solution of 2-trimethylphosphonoacrylate (12.6 mL, 81 mmol). After stirring at that temperature for an additional 30 min, the solution was warmed to room temperature and treated with a solution of formaldehyde (110 mmol) in water (37% formaldehyde in water, formalin 8.2 mL). The solution was allowed to stir at room temperature for 16 h and then concentrated in vacuo. The residue was dissolved in water and the aqueous phase extracted with ethyl acetate. The combined ethyl acetate extract was washed with brine, dried over anhyd $MgSO_4$, filtered and concentrated in vacuo to provide a clear oil that was purified by flash chromatography over silica gel eluting with ethyl acetate. The appropriate fractions were combined and concentrated to give a clear oil, 13.8 g, 82% that was suitable to be used directly in the next step.

Preparation of Methyl 2(S)-[(dimethylphosphoryl)methyl] propionate by Catalytic Asymmetric Hydrogenation.

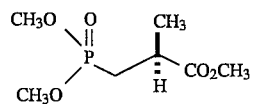

A solution of methyl 2[(dimethoxyphosphoryl)methyl] propenoate (13.8 g, 66 mmol) was dissolved in 50 mL of anhyd methanol and the solution thoroughly degassed with nitrogen or argon. This solution was then treated with rhodium (R, R)-DiPAMP catalyst (50 mg, 67 μmol) and placed in a Fisher-Porter bottle and again purged with nitrogen five times. Hydrogen was flushed through the bottle five times and the solution hydrogenated at 2.7 ATM for 18 h. The methanol was removed and the residue purified by flash chromatography on silica gel eluting with ethyl acetate to provide a slightly yellow oil that was further purified by vacuum distillation, 7.80 g, 56%, bp 50°–52° C. 0.2 mm Hg $[\alpha]_D$ at 25° C.=−8.80 (c=2.6, MeOH). $^1$H NMR (300 MHz, $CDCl_3$/TMS) δ3.72(d, J=10.8 Hz, 3H), 3.71(d, J=10.8 Hz, 3H), 3.69(s, 3H), 2.80(ddq, J=7.2, 7.0, 6.9 Hz, 1H), 2.28(ddd, J=7.0, 15.5, 15.5 Hz, 1H), 1.80(ddd, J=6.9, 15.5, 15.5 Hz, 1H), 1.28(d, J=7.2 Hz, 3H).

Preparation of Methyl 2(R,S)-[(dimethylphosphoryl)methyl] propionate by Catalytic Hydrogenation.

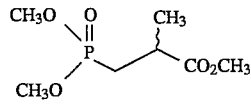

A small sample of methyl 2[(dimethoxyphosphoryl)methyl] propenoate (140 mg, 0.67 mmol) was dissolved in 10 mL of methanol and hydrogenated over 20 mg of 10% palladium on carbon for 3 h at 2.7 ATM and room temperature. The catalyst was removed by filtration through diatomaceous earth and the filtrate concentrated in vacuo to give the desired racemic product, 130 mg, 92%, as an oil.

Preparation of Dimethyl-2-(methoxycarbonyl)ethanephosphonate.

This procedure was reported by; Kreutzkamp, N.; Mengel, W. *Chem. Ber.*, 1967, 100, 709–714.

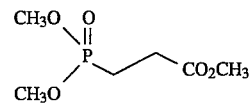

A mixture of methyl acrylate (30 mL, 28.7 g, 0.33 mol) and dimethylphosphite (36.7 g, 0.33 mol) was cooled to 0° C. and treated with a solution of sodium methoxide (1M) in methanol (5 mL). After a few min a vigorous exothermic reaction took place. When the reaction subsided, an additional portion of sodium methoxide was added. This procedure was repeated for a total of four times. The reaction was then allowed to stir at room temperature for 16 h and then the methanol removed by distillation. The residue was then vacuum distilled, bp 95° C. @ 0.15mm, to provide 45.6 g, 70% of pure product. $^1$H NMR ($CDCl_3$/TMS/300 MHz) δ3.71(d, J=11.1 Hz, 6H), 3.67 (s, 3H), 2.57 (td, J=8.4, 12.5 Hz, 2H), 2.06(td, J=8.4 12.5 Hz, 2H); $^{31}$P NMR ($CDCl_3$) 33.3 (s); $^{13}$C NMR ($CDCl_3$) 172.3, 52.3(d, J=6.5 Hz), 51.8, 27.0(d, J=4.1 Hz), 20.8, 18.9.

Preparation of Diethyl-2-(ethoxycarbonyl)ethanephosphonate.

This procedure was reported by; McConnel, R. L.; Coover, H. W., Jr. *J. Am. Chem. Soc.*, 1956, 78, 4453.

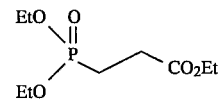

Diethyl-2-(ethoxycarbonyl)ethanephosphonate was obtained by the reaction of triethylphosphite with betapropiolactone.

Preparation of Ethyl 2(Z)-[(diethoxyphosphoryl)methyl]-4-methyl-2-pentenoate.

This procedure was reported by; Janecki, T.; Bodalski, R. Synthesis, 1989, 506–510.

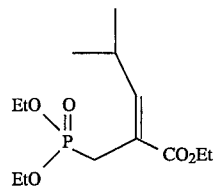

Part 1

A solution of diisopropylamine (3.9 mL, 27.8 mmol) in 40 mL of anhyd tetrahydrofuran (THF) was cooled to 0° C. and treated with n-butyllithium in hexanes (11.1 mL, 2.5M, 27.8 mmol) for 20 min. The solution was cooled to −78 ° C. and treated with a solution of diethyl-2-(ethoxycarbonyl)ethanephosphonate (6.0 g, 25.2 mmol) in 20 mL of THF dropwise via syringe over ca. 10 min. The mixture was maintained at −78° C. for 45 min and then treated with isobutyraldehyde (2.29 mL, 25.2 mmol) dissolved in 10 mL of THF. This mixture was stirred at low temperature for 15 min and then warmed to room temperature and stirred at this temperature for an additional 2 h and then the reaction was quenched by the addition of 50 mL of water. The solution was diluted with ether and the phases separated and the aqueous phase extracted with ether. The aqueous phase was acidified to pH=1 with conc HCl extracted with ether. The ethereal phase was washed with brine, dried over anhyd MgSO₄, filtered and concentrated in vacuo to provide a yellow oil, 5.65 g, 84% that was used directly in the next step.

Part 2

The product from Part 1 was dissolved in 25 mL of carbon tetrachloride and treated with thionyl chloride (2.1 mL, 29 mmol) at room temperature. The solution was stirred for 16 h at room temperature and then treated with ethanol for 1 h. The solution was then treated with saturated aqueous NaHCO₃ and the phases separated. The organic layer was dried over anhyd MgSO₄, filtered and concentrated in vacuo to give a brown oil, 5.70 g, that was purified by vacuum distillation, bp 110°–114° C., 0.15 mm, 2.43 g, 34% for two steps. ¹H NMR indicated that only the Z isomer had been obtained.

Preparation of Methyl 2(E) and (Z)-[(dimethoxyphosphoryl)methyl]-4-methyl-2-pentenoate.

This is an adapted procedure from; Martin, D. J.; Gordon, M.; Griffin, C. E. Tetrahedron, 1967, 23, 1831–1840.
Sodium (0.44 g, 19.3 gatom) was slowly dissolved in 45 mL of anhydrous methanol with stirring under nitrogen. To this solution was added dimethylphosphite (1.5 mL, 16.1 mmol) at 0° C. The solution was stirred at 0° C. for 30 min and then treated with dimethyl-2-(methoxycarbonyl)ethanephosphonate (4.7 g, 24.2 mmol) via syringe. After 30 min isobutryaldehyde (2.9 mL,

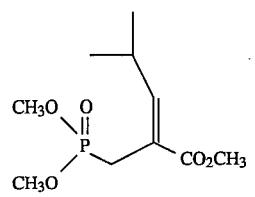

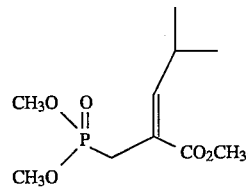

32.2 mmol) was added via syringe. This mixture was then stirred at room temperature for 16 h and then concentrated in vacuo. The residue was dissolved in ethyl acetate and washed with water, brine, dried over anhyd MgSO₄, filtered and concentrated in vacuo to give a clear oil that was purified by flash chromatography on silica gel to provide 3.0 g, 75% of pure product as an oil. ¹H NMR indicated that a 1:1 mixture of E:Z isomers had been formed.

Catalytic asymmetric hydrogenation of methyl 2(E) and (Z)-[(dimethoxyphosphoryl)methyl]-4-methyl-2-pentenoate: Preparation of methyl 2(S)-[(dimethoxyphosphryl)methyl-4-methyl-pentanoate.

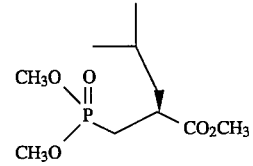

A sample of methyl 2(E) and (Z) [(dimethoxyphosphoryl)methyl]-4-methyl-2-pentenoate (9.61 g, 38.6 mmol) and rhodium (R,R)DiPAMP (100 mg, 0.13 mmol) were dissolved in 50 mL of degassed methanol and placed in a small Fisher-Porter bottle. The solution was flushed with nitrogen and then charged with hydrogen to a pressure of 2.7 ATM. The solution was then stirred for 40 h. The bottle was opened and the solvent removed under reduced pressure to give a 1:1 mixture of products. ¹H NMR examination revealed that the Z isomer had been converted to the desired product whereas the E isomer remained unchanged.

Preparation of Methyl 2(E) and (Z)-[(dimethoxyphosphoryl)methyl]-3-phenyl-2-propenoate: E selective method.

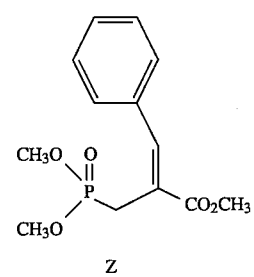

-continued

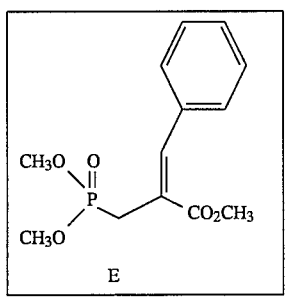

E

Dimethylphosphite (5.0 mL, 54 mmol) was dissolved in 130 mL of methanol cooled to 0° C. and then treated by the dropwise addition of a solution of sodium methoxide (65 mmol) in 150 mL of methanol. After the addition was complete, the solution was stirred at 0° C. for 15 min and then treated with a solution of 2-trimethylphosphonoacrylate (12.6 mL, 81 mmol). After stirring at that temperature for an additional 30 min, the solution was waned to room temperature and treated with a solution of benzaldehyde (11.2 mL, 110 mmol) in 20 mL of methanol. The solution was allowed to stir at room temperature for 3 h and then concentrated in vacuo. The residue was dissolved in water and the aqueous phase extracted with ethyl acetate. The combined ethyl acetate extract was washed with brine, dried over anhyd MgSO₄, filtered and concentrated in vacuo to provide a clear oil that was purified by chromatography on a Waters Prep-500 instrument on silica gel eluting with ethyl acetate. The appropriate fractions were combined and concentrated to give a clear oil, 12.3 g, 80%. $^1$H NMR indicated that a 5:1 ratio of E:Z isomers had been formed.

Catalytic asymmetric hydrogenation of methyl 2(E) and (Z) -[(dimethoxyphosphoryl)methyl]-3-phenyl-2-propenoate:

Preparation of methyl 2(S)-[dimethoxyphosphoryl)methyl]-3-phenyl-2-propenoate.

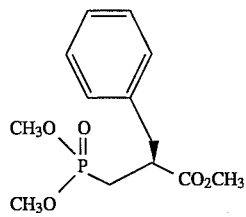

A sample of methyl 2(E) and (Z)-[ (dimethoxyphosphoryl)methyl]-3-phenyl-2-propenoate (E:Z ratio=5.1) (12.2 g, 43 mmol) and rhodium (R,R)DiPAMP (100 mg, 0.13 mmol) were dissolved in 50 mL of degassed methanol and placed in a small Fisher-Porter bottle. The solution was flushed with nitrogen and then charged with hydrogen to a pressure of 2.7 ATM. The solution was then stirred for 16 h. The bottle was opened and the solvent removed under reduced pressure to give a 5:1 mixture of products. $^1$H NMR examination revealed that the Z isomer had been converted to the desired product whereas the E isomer remained unchanged.

Preparation of Methyl 2(E) and-(Z)-[(dimethoxyphosphoryl)methyl]-3-phenyl-2-butenoate: Z selective method.

This procedure was reported by; Janecki, T.; Bodalski, R. Synthesis, 1990, 799–801.

Part 1: Preparation of methyl 2-[(1-hydroxy-1 -phenyl)methyl] 2-propenoate.

This procedure was reported by Hoffmann, H. M. R.; Rabe, J. Angew. Chem., Int. Ed. Engl., 1983, 22, 795.

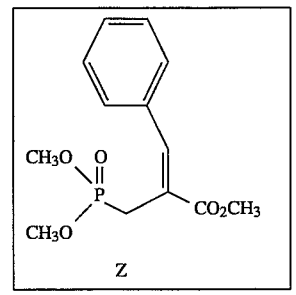

Z

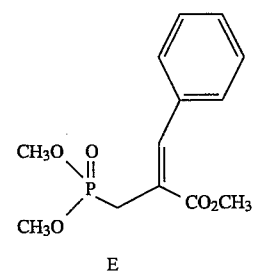

E

A mixture of benzaldehyde (0.1 mol), methyl acrylate (0.15 mol), and 1,4-diazabicyclo[2.2.2[octane (1.6 g, 0.015 mol) was allowed to stand at room temperature for 14 days and then concentrated in vacuo. The residue was dissolved in ether and washed with 3N HCl, saturated aqueous NaHCO₃, brine, dried over anhyd MgSO₄, filtered and concentrated in vacuo to provide a clear oil that was used directly in the next step without further purification.

Part 2

A solution of the alcohol from Part 2 (50 mmol) and triethylamine (5.05 g, 50 mmol) were dissolved in 100 mL of ether and treated with diethyl phosphorochloridite (7.82 g, 50 mmol) at −10° C. The solution was maintained at that temperature for 1 h and then the precipitated triethylammonium hydrochloride was removed by filtration. The filtrate was concentrated in vacuo and warmed in an oil bath at 80° C. for 3 h. The residue was cooled to room temperature and diluted with ether and then washed with 3N HCl, saturated aqueous NaHCO₃, brine, dried over anhyd MgSO₄, filtered and concentrated in vacuo to provide a clear oil that was purified by vacuum distillation, to provide 9.7 g, 68% of product, bp 130°–131° C. 0.05 min. $^1$H NMR indicated that a 19:1 mixture of Z:E isomers had been formed.

What is claimed is:

1. Process for the preparation of a compound represented by the formula

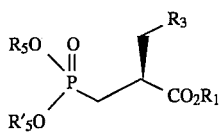

(I)

wherein $R_1$ is hydrogen, alkyl, lower cycloalkyl, $CH_2Ar$ or Ar radicals, wherein Ar is an aromatic group;

$R_3$ is
(1) hydrogen radical;
(2) alkyl radical of from one to six carbon atoms or alkyl radical of from one to six carbon atoms substituted by one or two hydroxyl, chloro or fluoro radicals;
(3) cycloalkyl of from three to seven ring carbon atoms;
(4) phenyl or phenyl substituted by one to three radicals selected from the group consisting of alkyl of from one to four carbons, fluoro, chloro, bromo, iodo, alkoxy of from one to three carbon atoms, nitro, amido, hydroxy, and mono- and dialkylamido of from one to four alkyl carbon atoms;
(5) tolyl or tolyl substituted by one to three radicals selected from the group consisting of alkyl of from of one to four carbon atoms, fluoro, chloro, bromo, iodo, alkoxy of from one to three carbon atoms, nitro, amido, hydroxy, and mono- and dialkylamido of from one to four alkyl carbon atoms;
(6) naphthyl or naphthyl substituted by one to three radicals selected from the group consisting of alkyl of from of one to four carbon atoms, fluoro, chloro, bromo, iodo, alkoxy of from one to three carbon atoms, nitro, amido, hydroxy, and mono- and dialkylamido of from one to four alkyl carbon atoms;
(7) indol-3-yl, indol-2-yl, imidazoly-4-yl, indol-3-ylmethyl, indol-2-ylmethyl or imidazol-4-ylmethyl radicals;
(8) NHA wherein A is selected from the group consisting of
hydrogen;
trityl;
alkyl of from one to six carbon atoms;
alkyl of from one to six carbon atoms substituted with hydroxyl, chloro or fluoro;
phenyl, naphthyl or phthaloyl unsubstituted or substituted by one to three substituents selected from the group consisting of alkyl of from of one to three carbon atoms, fluoro, chloro, bromo, iodo, alkoxy of from one to three carbon atoms, nitro, amido, hydroxy, and mono- and dialkylamido of from one to four carbon atoms;
indolyl; pyridyl; furyl; benzisoxazolyl;
$R_{12}(R_{13}R_{14}C)_m CO$ wherein m is an integer from one to three and $R_{12}$, $R_{13}$, and $R_{14}$ are each independently selected from the group consisting of hydrogen; alkyl of from of one to three carbon atoms; alkyl of from of one to three carbon atoms substituted by chloro, fluoro or hydroxy; fluoro; chloro; hydroxy; alkoxy of from one to three carbon atoms; amido; and mono- and dialkylamido of from one to four carbon atoms; phenyl and phenyl substituted by one to three substituents selected from the group consisting of alkyl of from of one to three carbon atoms, fluoro, chloro, bromo, iodo, alkoxy of from one to three carbon atoms, nitro, amido, hydroxy, and mono- and dialkylamido of from one to four carbon atoms; naphthyl and naphthyl substituted by one to three substituents selected from the group consisting of alkyl of from of one to three carbon atoms: fluoro, chloro, bromo, iodo, alkoxy of from one to three carbon atoms, nitro, amido, hydroxy, and mono- and dialkylamido of from one to four carbon atoms;
pyridyl; furyl; benzisoxazolyl; and $R_{12}$, $R_{13}$ and $R_{14}$ are indepently joined to form a monocyclic, bicyclic and tricycle ring system wherein each ring is a cycloalkyl of from three to six carbons; with the proviso that only one of $R_{12}$, $R_{13}$, and $R_{14}$ can be hydroxy or alkoxy on the same carbon and can not be hydroxy, chloro or fluoro when m is one;
$R_{12}(R_{13}R_{14}C)_m W$ wherein W is OCO or $SO_2$ and m, $R_{12}$, $R_{13}$ and $R_{14}$ are independently as defined above;
$R_{20}W$ wherein W is as defined above and $R_{20}$ is ispyridyl, furyl or benzisoxazolyl;
$R_{21}W$ wherein $R_{21}$ is phenyl or naphthyl unsubstituted or substituted by from one to three substituents selected from the group consisting of alkyl of from of one to three carbon atoms, fluoro, chloro, bromo, iodo, alkoxy of from one to three carbon atoms, nitro, amido, hydroxy, and mono- and dialkylamido of from one to four carbon atoms;
$R_{12}(R_{13}R_{14}C)_m P(O)(OR_{22})$ wherein $R_{22}$ is alkyl of from one to four carbons or phenyl and m, $R_{12}$, $R_{13}$ and $R_{14}$ are as defined above;
$R_{20}P(O)(OR_{22})$ wherein $R_{20}$ and $R_{22}$ are as defined above;
$R_{21}P(O)(OR_{22})$ wherein $R_{21}$ and $R_{22}$ are as defined above;
(9) $R_{12}(R_{13}R_{14}C)_m V$ wherein V is O or NH and m, $R_{12}$, $R_{13}$ and $R_{14}$ are independently as defined above;
(10) $N(R_{11})_2$ wherein $R_{11}$ is alkyl of from one to four carbon atoms;
(11) azetidinyl, pyrrolidinyl, piperidinyl, or morpholinyl radicals;
(12) $R_{17}OCH_2O$ wherein $R_{17}$ is
(a) alkyl of from one to six carbon atoms,
(b) $R_{21}$ wherein $R_{21}$ is independently defined as above, or
(c) $CH_2Q_1$ wherein $Q_1$ is phenyl, naphthyl or a 5 to 7 membered heterocycle;
(13) $R_{17}OCH_2CH_2OCH_2$ wherein $R_{17}$ is independently as defined above;
(14) alkynyl of from two to six carbon atoms optionally substituted with $R_{21}$ wherein $R_{21}$ is independently as defined above;
(15) alkenyl of from two to six carbon atoms optionally substituted with $R_{21}$ where in $R_{21}$ is independently as define above; or
(16) the side chain of an amino acid selected from the group consisting of aspargine, S-methyl cysteine and the corresponding sulfoxide and sulfone derivatives thereof, leucine, isoleucine, allo-isoleucine, tert-leucine, alanine, phenylalanine, ornithine, histidine, norleucine, glutamine, valine, threonine, allothreonine, serine, aspartic acid and betacyanoalanine; and $R_5$ and $R'_5$ are each independently hydrogen, alkyl, lower cycloalkyl or Ar wherein Ar is an aromatic group;
wherein said process comprises treating a compound represented by the formula

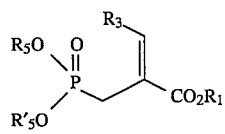

or isomeric mixtures thereof, wherein $R_1$, $R_3$, $R_5$ and $R'_5$ are as defined above, with hydrogen in the presence of rhodium (R,R)-(1,2-ethanediyl bis[ orthomethoxyphenyl)phenylphosphine] in deoxygenated solvent; and optionally hydrolyzing the phosphous or carbon containing acid group.

2. Process of claim 1 for the preparation of a compound represented by formula (I) wherein $R_1$ is hydrogen, alkyl of from one to four carbon atoms, cycloalkyl of three to seven ring carbon atoms, or phenylmethyl radicals;

$R_3$ is
- (1) hydrogen radical;
- (2) alkyl radical of from one to six carbon atoms or alkyl radical of from one to six carbon atoms substituted by one or two hydroxyl, chloro or fluoro radicals;
- (3) cycloalkyl radical of from three to seven ring carbon atoms;
- (4) phenyl radical or phenyl radical substituted by one to three radicals selected from the group consisting of alkyl of from one to four carbons, fluoro, chloro, bromo, iodo, alkoxy of from one to three carbon atoms, nitro, amido, hydroxy, and mono- and dialkylamido of from one to four carbon atoms;
- (5) tolyl radical or tolyl radical substituted by one to three radicals selected from the group consisting of alkyl of from of one to four carbon atoms, fluoro, chloro, bromo, iodo, alkoxy of from one to three carbon atoms, nitro, amido, hydroxy, and mono- and dialkylamido of from one to four carbon atoms;
- (6) naphthyl radical or naphthyl radical substituted by one to three radicals selected from the group consisting of alkyl of from of one to four carbon atoms, fluoro, chloro, bromo, iodo, alkoxy of from one to three carbon atoms, nitro, amido, hydroxy, and mono- and dialkylamido of from one to four carbon atoms; or
- (7) indol-3-yl, indol-2-yl, imidazoly-4-yl, indol-3 -ylmethyl, indol-2-ylmethyl or imidazol-4 -ylmethyl radicals; and $R_5$ and $R'_5$ are each independently hydrogen, alkyl of from one to four carbon atoms, cycloalkyl of three to seven ring carbon atoms, or phenylmethyl radicals.

3. Process of claim 2 for the preparation of a compound represented by formula (I) wherein $R_1$ is hydrogen, alkyl of from one to four carbon atoms, or phenylmethyl radicals;

$R_3$ is hydrogen, alkyl of from one to six carbon atoms, cycloalkyl of from three to seven ring carbon atoms, phenyl, tolyl, or naphthyl radicals; and $R_5$ and $R'_5$ are each independently hydrogen, alkyl of from one to four carbon atoms, or phenylmethyl radicals.

4. Process of claim 1 wherein said compound of formula (I) is methyl 2(S)-[(dimethoxyphosphoryl)methyl] propionate.

5. Process of claim 1 wherein said compound of formula (I) is methyl 2(S)-[(dimethoxphosphoryl)methyl]-4 methylpentanoate.

6. Process of claim 1 wherein said compound of formula (I) is methyl 2(S)-[(dimethoxyphosphoryl)methyl]-3 -phenylpropionate.

* * * * *